United States Patent [19]

Pearson et al.

[11] Patent Number: 6,057,288
[45] Date of Patent: May 2, 2000

[54] AUTOINDUCER MOLECULE

[75] Inventors: James P. Pearson; Kendall M. Gray, both of Iowa City, Iowa; Luciano Passador, Rochester, N.Y.; Kenneth D. Tucker, Germantown, Md.; Anatol Eberhard, Brooktondale; Barbara H. Iglewski, Fairport, both of N.Y.; Everett P. Greenberg, Iowa City, Iowa

[73] Assignees: University of Iowa, Iowa City, Iowa; University of Rochester, Rochester; Ithaca College, Ithaca, both of N.Y.

[21] Appl. No.: 08/456,864

[22] Filed: Jun. 1, 1995

Related U.S. Application Data

[62] Division of application No. 08/104,487, Aug. 9, 1993, Pat. No. 5,591,872.

[51] Int. Cl.$^7$ .............................. A01N 37/18; C07K 1/00; C12N 1/00

[52] U.S. Cl. .............................. 514/2; 514/851; 530/350; 435/875

[58] Field of Search ........................ 514/2, 851; 530/350; 435/875

[56] References Cited

FOREIGN PATENT DOCUMENTS

WO 92/18614  10/1992  WIPO.

OTHER PUBLICATIONS

Bainton, et al., "A general role for the lux autoinducer in bacterial cell signalling: control of antibiotic biosynthesis in Erwinia," *Gene*, 1992, vol. 116, 87–91.

Bainton, et al., "N-(3-Oxohexanoyl)-L-homoserine lactose regulates carbapenem antibiotic production in *Erwinia carotovora*," *Biochemistry Journal*, 1992, vol. 288, 997–1004.

Bever, et al., "Molecular Characterization and Nucleotide Sequence of the *Pseudomas aeruginosa* Elastase Structural Gene," *Journal of Bacteriology*, 1988, vol. 170, No. 9, 4309–4314.

Cao, et al., "Biosynthesis and Stereochemistry of the Autoinducer Controlling Luminescence in *Vibrio harveyi*," *Journal of Bacteriology*, 1993, vol. 175, No. 12, 3856–3862.

Cao, et al., "Purification and Structural Identification of an Autoinducer for the Luminescence System of *Vibrio harveyi*," *Journal of Biological Chemistry*, 1989, vol. 264, No. 36, 21670–21676.

Choi, et al., "Genetic Dissection of DNA Binding and Luminescence Gene Activation by the *Vibrio fischeri* LuxR Protein," *Journal of Bacteriology*, 1992, vol. 174, No. 12, 4064–4069.

Eberhard, et al., "Analogs of the autoinducer of bioluminescence in *Vibrio fischeri*," *Archives of Microbiology*, 1986, vol. 146, No. 35, 35–40.

Eberhard, et al., "Structural Identification of Autoinducer of *Photobacterium fischeri* Luciferase," *Biochemistry*, 1981, vol. 20, 2444–2449.

Eberhard, et al., "Synthesis of the lux gene autoinducer in *Vibrio fischeri* is positively autoregulated," *Archives of Microbiology*, 1991, vol. 155, 294–297.

Gambello and Iglewski, "Cloning and Characterization of the *Pseudomonas aeruginosa* lasR Gene, a Transcriptional Activator of Elastase Expression," *Journal of Bacteriology*, 1991, vol. 173, No. 9, 3000–3009.

Goswami, et al., "Microbial Hydroxylation of Quadrone to 8a–Hydroxyquadrone," *Journal of Natural Products*, 1987, vol. 50, No. 1, 49–54.

Hoiby, "*Pseudomonas Aeruginosa* Infection in Cystic Fibrosis," *Acta. Path. Microbiol. Scand. Sect. B.*, 1974, vol. 82, 551–558.

Iglewski and Kabat, "NAD–Dependent Inhibition of Protein Synthesis by *Pseudomonas aeruginosa* Toxin," *PNAS*, 1975, vol. 72, 2284–2288.

Iglewski, et al., "*Pseudomonas aeruginosa* exoenzyme S: An adenosine diphosphate ribosyltransferase distinct from toxin A," *PNAS* 1978, vol. 75, No. 7, 3211–3215.

Jones, et al., "The lux autoinducer regulates the production of exoenzyme virulence in *Erwinia carotovora* and *Pseudomonas aeruginosa*," *EMBO Journal*, 1993, vol. 12, No. 6, 2477–2482.

Kaplan and Greenberg, "Diffusion of Autoinducer is Involved in Regulation of the *Vibrio fischeri* Luminescence System," *Journal of Bacteriology*, 1985, vol. 163, 1210–1214.

Kessler and Safrin, "Synthesis, Processing and Transport of *Pseudomonas aeruginosa* Elastase," *Journal of Bacteriology*, 1988, vol. 170, No. 11, 5241–5247.

Meighen, "Molecular Biology of Bacterial Bioluminescence," *Microbiological Reviews*, 1991, vol. 55, No. 1, 123–142.

Nicas and Iglewski, "The Contribution of exoproducts to virulence of *Pseudomonas aeruginosa*," *Canadian Journal of Microbiology*, 1985, vol. 31, No. 4, 387–392.

Passador, et al., "Expression of *Pseudomas aeruginosa* Virulence Genes Requires Cell–to–Cell Communication," *Science*, 1993, vol. 260, 1127–1130.

Pearson, et al., "Structure of the autoinducer required for expression of *Pseudomonas aeruginosa* virulence genes," *PNAS USA*, 1994, vol. 91, No. 1, 197–201.

Piper, et al., "Conjugation factor of *Agrobacterium tumefaciens* regulates Ti plasmid transfer by autoinduction," *Nature*, 1993, vol. 362, 448–450.

(List continued on next page.)

*Primary Examiner*—Nita Minnifield
*Assistant Examiner*—Padma Baskar
*Attorney, Agent, or Firm*—Lahive & Cockfield, LLP; Elizabeth A. Hanley, Esq.; Peter C. Lauro, Esq.

[57] ABSTRACT

Autoinducer molecules, e.g., N-(3-oxododecanoyl) homoserine lactone, for *Pseudomonas aeruginosa* are described. The molecules regulate gene expression in the bacterium. Therapeutic compositions and therapeutic methods involving analogs and/or inhibitors of the autoinducer molecules also are described. The molecules are useful for treating or preventing infection by *Pseudomonas aeruginosa*.

5 Claims, 2 Drawing Sheets

OTHER PUBLICATIONS

Pirhonen, et al., "A small diffusible signal molecule is responsible for the global control of virulence and exoenzyme production in the plant pathogen *Erwinia carotovora*," *EMBO Journal*, 1993, vol. 12, No. 6, 2467–2476.

Railing, et al., "Growth rate–dependent regulation of RNA polymerase synthesis in *Escherichia coil*," *Mol. Gen. Genet.*, 1985, vol. 201, 379–386.

Reynolds, et al., "*Pseudomonas aeruginosa* Infections: Persisting Problems and Current Research to Find New Therapies," *Annals of Internal Medicine*, 1975, vol. 82, No. 6, 819–831.

Stewart, et al., "Shedding New Light On Food Microbiology," *ASM News*, 1993, vol. 59, No. 5, 241–247.

Wierenga and Skulnick, "General, Efficient, One–Step Synthesis of β–Keto Esters," *Journal of Organic Chemistry*, 1979, vol. 44, No. 2, 310–311.

Williams, et al., "Small molecule–mediated density–dependent control of gene expression in prokaryotes: Bioluminescence and the biosynthesis of carbapenem antibiotic," *FEMS Microbiology*, 1992, vol. 100, 161–168.

Zhang, et al., "Agrobacterium conjugation and gene regulation by N–acyl–L–homoserine lactones," *Nature*, 1993, vol. 362, 446–448.

AUTOINDUCER MOLECULE

This application is a divisional application of Ser. No. 08/104,487 filed on Aug. 9, 1993, now U.S. Pat. No. 5,591,872. The contents of all of the aforementioned application(s) are hereby incorporated by reference.

GOVERNMENT SUPPORT

This research was supported by grants and fellowships from the Cystic Fibrosis Foundation, Office of Naval Research (N00014-80-6570), National Institute of Allergy and Infectious Diseases (33713), and National Science Foundation (DIR9017262).

BACKGROUND

The Gram-negative bacterium *Pseudomonas aeruginosa* is an opportunistic human pathogen that causes infections in immunocompromised hosts, and colonizes the lungs of individuals with cystic fibrosis (Hoiby, N. (1974) *Acta Patholgica Microbiol. Scand.* Sect. B. 82, 551–558; Reynolds, H. Y., Levine, A. S., Wood, R. E., Zierdt, C. H., Dale, D. C. and Pennington, J. L. (1975) *Ann. Intern. Med.* 82, 819–832). This bacterium produces a number of extracellular virulence factors including exotoxin A, which is encoded by the toxA gene (Iglewski, B. H. and Kabat, D. (1975) *Proc. Natl. Acad. Sci. USA.* 72, 22842288; Iglewski, B. H., Sadoff, J. C., Bjorn, M. J., and Maxwell, E. S. (1978) *Proc. Natl. Acad. Sci. USA.* 75, 3211–3215), two elastolytic proteases, encoded by the lasA and lasB genes, and an alkaline protease encoded by the aprA gene (Morihara, K. and Homma, J. Y. (1985) in *Bacterial Enzymes and Virulence*, ed. Holder, I. A. (CRC Press, Boca Raton, Fla.) pp. 41–79; Bever, R. A. and Iglewski, B. H. (1988) *J. Bacteriol.* 170, 4309–4313; Kessler, E. and Saffrin, M. (1988) *J. Bacteriol.* 170, 5241–5247).

Autoinducer molecules are capable of regulating the gene expression of certain microorganisms. Bycroft et al. (WO92/18614) describe a class of autoinducer molecules which includes N-($\beta$-ketocaproyl) L-homoserine lactone and N-($\beta$-hydroxybutyryl) homoserine lactone. All of the exemplified autoinducer molecules of Bycroft et al. contain $C_1$–$C_7$ side chains. However, autoinducer molecules with side chains of greater length or cyclic side chains are not exemplified by Bycroft et al.

Bycroft et al. state that *Pseudomonas aeruginosa* is affected by N-($\beta$-ketocaproyl) homoserine lactone. As recently as 1993, researchers have believed that N-($\beta$-ketocaproyl) homoserine lactone is the autoinducer molecule of *P. aeruginosa*. (Stewart, G. S. A. B. and P. Williams (1993) *ASM News*, 59, 241–46).

SUMMARY OF THE INVENTION

The present invention is based, in least in part, on the discovery that the autoinducer molecule for *Pseudomonas aeruginosa* is N-(3-oxododecanoyl)homoserine lactone and not N-($\beta$-ketocaproyl)homoserine lactone as previously believed. Upon the discovery of this novel autoinducer molecule, it was realized that autoinducer molecule(s) containing a fatty moiety or a moiety having at least seven members in the R moiety of the formula set forth below:

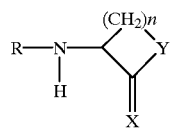

are involved in the regulation of gene expression. In the above formula, n is 2 or 3; Y is O, S, or NH; X is O, S, or NH; and R is a fatty hydrocarbon or acyl moiety that may be substituted or a moiety having at least seven members containing a ring structure that may be substituted. The present invention further pertains to autoinducer molecules of the following formula:

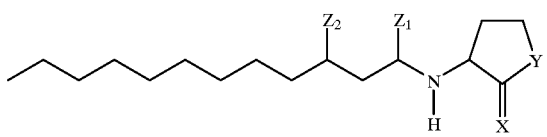

wherein X and Y are as defined above and $Z_1$ and $Z_2$ are independently selected from the group consisting of hydrogen, =O, =S, and =NH.

The present invention also pertains to analogs of the autoinducer molecule that affect the activity of the LasR protein, e.g., inhibit the autoinducer activity or synergistically enhance the autoinducer activity. The present invention even further includes inhibitors of the autoinducer activity of N-(3-oxododecanoyl)homoserine lactone. The present invention also pertains to methods of selecting such inhibitors and analogs. These methods involve the contact of the autoinducer molecule with the suspected inhibitor or synergist followed by the measuring of the ability of the treated autoinducer molecule to perform its intended function. From these steps, it is determined whether the suspected inhibitor or synergist inhibits or enhances the ability of the autoinducer molecule to stimulate the activity of the selected gene.

The present invention also pertains to therapeutic compositions comprising an agent having the ability to inhibit the activity of the LasR protein of *Pseudomonas aeruginosa* and/or inhibit the autoinducer activity of N-(3-oxododecanoyl)homoserine lactone and a pharmaceutically acceptable carrier. The agent can be the analogs or inhibitors as described above and in further detail below.

The present invention even further pertains to a method of inhibiting the infectivity of *Pseudomonas aeruginosa* and a method of treating an immunocompromised individual infected with *Pseudomonas aeruginosa*. Both of these methods involve the administration to an individual of a therapeutically effective amount of the agents and/or therapeutic compositions described above that inhibit the activity of the LasR protein and/or inhibit the autoinducer activity of N-(3-oxododecanoyl)homoserine lactone. An example of an immunocompromised individual in an individual afflicted with cystic fibrosis.

The present invention further pertains to a culture medium containing as an added compound an autoinducer molecule as described and methods of controlling the expression of a gene in bacteria or cells using the described autoinducer molecules and/or analogs or inhibitors thereof.

The present invention also pertains to analogs of the autoinducer molecule that inhibit the induction of virulence factors by the autoinducer molecule or LasR. The virulence factors include exotoxin A, elastolytic proteases, and an alkaline protease.

DETAILED DESCRIPTION

Figure 1:
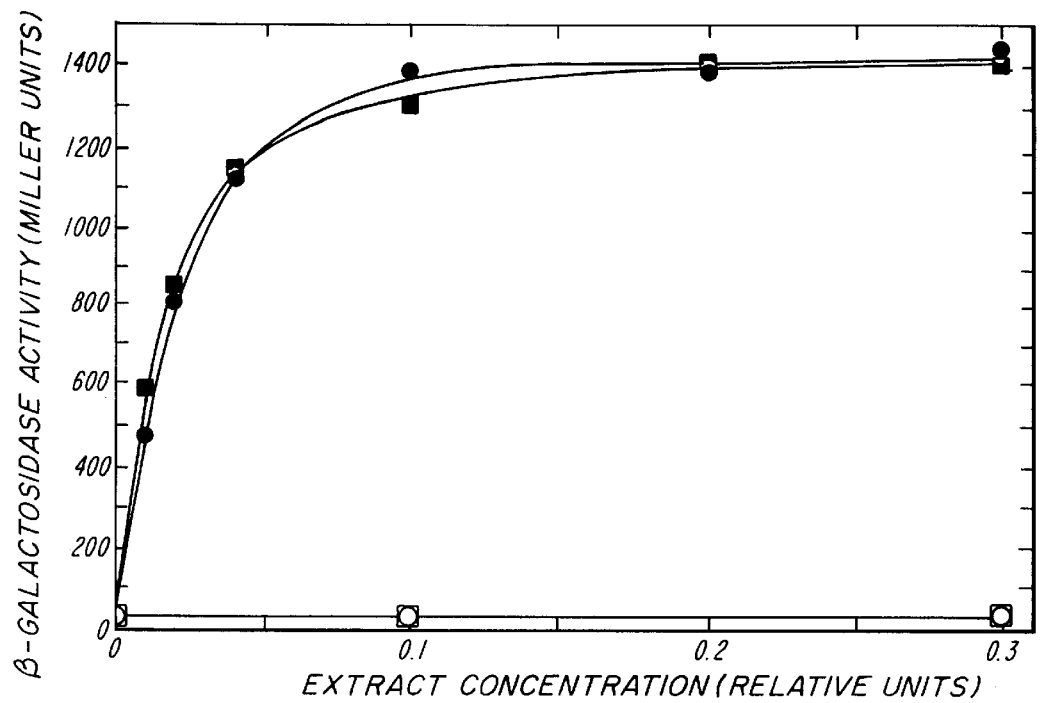
FIG. 1 shows the dose-response curve for *P. aeruginosa* autoinducer in ethyl acetate extracts of bacterial culture fluid. Culture fluid extracts were of *P. aeruginosa* PAO1 (●), *P. aeruginosa* PAO1-RI (○), *E. coli* with pLasI-1 (■), and *E. coli* without pLasI-1 (□). As defined in *Materials and Methods*, a unit of autoinducer activity is that amount required for half-maximal activation of the lasB promoter in *E. coli* (pKDT17).

The present invention pertains to autoinducer molecules of the formula:

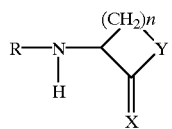

wherein n is 2 or 3; Y is O, S, or NH; X is O, S, or NH; and R is a fatty hydrocarbon or acyl moiety that may be substituted or a moiety having at least seven members containing a ring structure that may be substituted. The autoinducer molecule regulates the activity of the LasR protein of *Pseudomonas aeruginosa*. In addition, the present invention pertains to optically active isomers of the autoinducer molecule. The autoinducer molecule can be purified from the native source using conventional techniques or can be derived synthetically by chemical means. Included in the invention are optically active isomers of the claimed autoinducer molecule as well as analogs of the claimed autoinducer molecule.

The language "autoinducer molecule" is intended to include a molecule involved in the regulation of gene expression, e.g., it may increase or decrease gene expression, of a microorganism. Typically, autoinducer molecules are produced by microorganisms, such as bacteria, during metabolism. The autoinducer molecules then regulate gene expression, for example, by combining with a transcriptional activator protein.

The language "fatty hydrocarbon or acyl moiety" is intended to include a long straight or branched chain moiety having seven or more carbon atoms. For example, the fatty acyl moiety can be of the following formula:

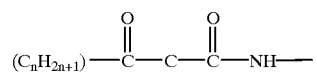

wherein n is 4 or more. The preferred fatty acyl moieties include $C_7$–$C_{14}$ acyl moieties, more preferred are $C_{10}$–$C_{14}$ acyl moieties, and most preferred is the $C_{12}$ acyl moiety. Fatty hydrocarbon or acyl moieties include saturated and unsaturated moieties as well as substituted moieties, for example, by substituting a S for an O. Examples of fatty hydrocarbon moieties include fatty alkyl, fatty alkenyl, and fatty alkynyl moieties.

The language "ring structure" is intended to include arrangements of atoms which form one or more rings. The ring structures can contain heterocyclic ring(s), e.g., oxygen, sulfur, or nitrogen containing, or can contain carbocyclic ring(s). The ring structure further can be a fused ring system. Examples of ring structures include 5 to 7 membered heterocyclic rings, napthyl, and phenyl. The ring structures further can be substituted with groups that do not effect the molecule's ability to perform its intended function as described above.

The substituents on the "R" moiety are substituents which do not detrimentally effect the molecule's ability to perform its intended autoinducer function. Examples of such substituents include hydrocarbon groups, e.g., lower alkyl, alkenyl and alkynyl groups, keto groups and halogen containing substituents. Examples of such substituents include butyl, propyl, methyl, butenyl, propenyl and butynyl groups.

The language "able to regulate the activity" is intended to include the activation of or an act to increase the operation of another molecule, e.g., the LasR protein.

The language "LasR protein of *Pseudomonas aeruginosa*" is intended to include the transcriptional activator proteins of the bacteria *Pseudomonas aeruginosa*. LasR proteins of *P. aeruginosa* include proteins encoded by the lasR gene of *P. aeruginosa*. The LasR proteins are global regulators of genes involved in the virulence of *P. aeruginosa*.

The language "isomer" is intended to include molecules having the same molecular formula as the autoinducer molecule but possessing different chemical and physical properties due to a different arrangement of the atoms in the molecule. Isomers include both optical isomers and structural isomers.

The language "optically active" is intended to include molecules that have the ability to rotate a plane of polarized light. An optically active isomer includes the L-isomer and the D-isomer of the claimed autoinducer molecule. The L-isomer of N-(3-oxododecanoyl)homoserine lactone is the active form. The D-isomer shows a small amount of activity and can inhibit the ability of the L-isomer to activate the LasR protein by attaching to the autoinducer binding domain of the LasR protein.

The language "purified from the native source" is intended to include an autoinducer molecule of the above formula that has been manufactured by an organism. "Purified from the native source" includes isolating the autoinducer molecule from the culture media or cytoplasm of bacteria such as *Pseudomonas aeruginosa* using conventional techniques.

The language "synthesized by chemical means" is intended to include autoinducer molecules of the claimed formula that have been made artificially outside of an organism. The invention includes the claimed autoinducer made by a scientist in a laboratory from chemical precursors using standard chemical synthesis techniques. For example, the claimed autoinducer molecules can be synthesized using the protocol of Eberhard et al. (Eberhard, A., Burlingame, A. L., Eberhard, C., Kenyon, G. L., Nealson, K. H. and Oppenheimer, N. J. (1981) *Biochemistry* 20, 2444–2449) from commercially available precursors. The starting materials can be modified to produce the desired end product.

The present invention further pertains to autinducer molecules of the following formula:

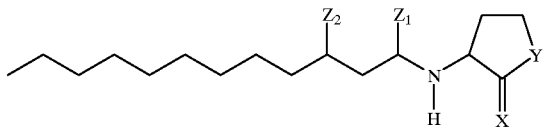

wherein X and Y are as defined above and $Z_1$ and $Z_2$ are independently selected from the group consisting of hydrogen, =O, =S, and =NH.

The preferred autoinducer molecule of the present invention is of the formula:

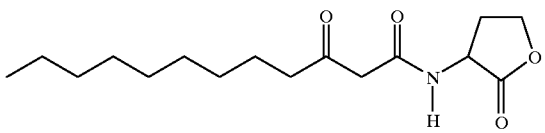

This autoinducer molecule is a novel chemical compound which is at least part of the present invention. The new chemical compound has utility as an autoinducer and also may have other utilities. As an autoinducer, it can regulate the activity of the transcriptional protein of *Pseudomonas aeruginosa*, LasR. The chemical name of the autoinducer molecule is N-(3-oxododecanoyl)homoserine lactone. The autoinducer molecule can be purified from the native source or can be derived synthetically by chemical means. Included in the invention are optically active isomers of the claimed autoinducer molecule as well as analogs of the claimed autoinducer molecule.

The language "analog" is intended to include molecules that are structurally similar but not identical to the claimed autoinducer molecule N-(3-oxododecanoyl)homoserine lactone. For example, the length of the fatty acyl moiety can be varied producing an analog or one of the keto groups can be removed from the fatty acyl moiety. Analogs include autoinducer molecules that are structurally similar to the claimed autoinducer molecule but can inhibit rather than stimulate the activity of the LasR protein or analogs which act synergistically to enhance the ability of the claimed autoinducer to increase the activity of the LasR protein. One of ordinary skill in the art would be able to select analogs which are useful within the present invention using the selection methods described below.

The present invention also pertains to methods of selecting inhibitors or synergists of the autoinducer molecule, N-(3-oxododecanoyl)homoserine lactone. The method comprises contacting the autoinducer molecule with a suspected inhibitor or synergist, measuring the ability of the treated autoinducer molecule to stimulate the activity of a selected gene then determining whether the suspected inhibitor or synergist represses or enhances the activity of the autoinducer molecule. Actual inhibitors and synergists of the autoinducer molecule are then selected. For example, a suspected inhibitor can be mixed with N-(3-oxododecanoyl)homoserine lactone and the mixture then combined with *E. coli* MG4 which produces β-galactosidase in the presence of N-(3-oxododecanoyl)homoserine lactone. The amount of β-galactosidase can then be compared to a standard to determine if the suspected inhibitor represses the ability of N-(3-oxododecanoyl)homoserine lactone to stimulate the production of β-galactosidase in *E. coli* MG4.

The language "inhibitors of the autoinducer molecule of *P. aeruginosa*" is intended to include molecules that interfere with the ability of the autoinducer molecule to stimulate the activity of the LasR protein of *P. aeruginosa*. Inhibitors include molecules that degrade or bind to N-(3-oxododecanoyl)homoserine lactone. The inhibitors can compete with the autoinducer molecule not allowing it to perform its intended function.

The language "synergist of the autoinducer molecule of *P. aeruginosa*" is intended to include molecules that enhance the ability of the autoinducer molecule to stimulate the LasR protein. Synergists include molecules that bind to either N-(3-oxododecanoyl)homoserine lactone or the LasR protein.

The present invention also pertains to methods of selecting inhibitory and synergistic analogs of the claimed autoinducer. The method comprises mixing a known amount of the autoinducer molecule with a known amount of the suspected inhibitory or synergistic analog, measuring the ability of the treated autoinducer molecule to stimulate the activity of a selected gene then determining whether the suspected inhibitory or synergistic analog represses or enhances the activity of the autoinducer molecule. Actual inhibitory or synergistic analogs of the autoinducer molecule are then selected.

The present invention further pertains to methods of inhibiting the infectivity of *P. aeruginosa*, methods for treating an immunocompromised host infected by *P. aeruginosa*, e.g., a person afflicted with cystic fibrosis, as well as therapeutic compositions. The methods comprise administering to an individual a therapeutically effective amount of an agent that is capable of inhibiting the activity of the LasR protein.

The language "inhibiting the infectivity of *P. aeruginosa*" is intended to include methods of affecting the ability of *P. aeruginosa* to initially infect or further infect an organism. This includes using agents that prevent the LasR protein from activating the transcription of extracellular virulence factors such as exotoxin A and elastolytic proteases by *P. aeruginosa*.

The language "agent" is intended to include molecules that inhibit the ability of the LasR protein to activate transcription of extracellular virulence factors. Agents include inhibitors of N-(3-oxododecanoyl)homoserine lactone. Agents also include analogs of N-(3-oxododecanoyl) homoserine lactone that can directly inhibit the LasR protein of *P. aeruginosa* or can compete with N-(3-oxododecanoyl) homoserine lactone. Inhibitory agents can be selected using the method described above.

The language "administering a therapeutically effective amount" is intended to include methods of giving or applying an agent to an organism which allow the agent to perform its intended therapeutic function. The therapeutically effective amounts of the agent will vary according to factors such as the degree of infection in the individual, the age, sex, and weight of the individual, and the ability of the agent to inhibit the activity of the LasR protein of *P. aeruginosa* in the individual. Dosage regima can be adjusted to provide the optimum therapeutic response. For example, several divided doses can be administered daily or the dose can be proportionally reduced as indicated by the exigencies of the therapeutic situation. Administering also includes contacting the agent with the LasR protein outside of an organism such as with a culture of bacteria.

The agent can be administered in a convenient manner such as by injection (subcutaneous, intravenous, etc.), oral administration, inhalation, transdermal application, or rectal administration. Depending on the route of administration, the agent can be coated with a material to protect the agent from the action of enzymes, acids and other natural conditions which may inactivate the agent.

The agent can also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the agent in the required amount in an appropriate solvent with one or a combination of ingredients enumerated above, as required, followed by filtered sterilization. Generally, dispersions are prepared by incorporating the agent into a sterile vehicle which contains a basic dispersion medium and the required other ingredients from those enumerated above.

The agent can be orally administered, for example, with an inert diluent or an assimilable edible carrier. The agent and other ingredients can also be enclosed in a hard or soft shell gelatin capsule, compressed into tablets, or incorporated directly into the individual's diet. For oral therapeutic administration, the agent can be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations can, of course, be varied and can conveniently be between about 5 to about 80% of the weight of the unit. The amount of agent in such therapeutically useful compositions is such that a suitable dosage will be obtained.

The tablets, troches, pills, capsules and the like can also contain the following: a binder such as gum gragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the agent, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the agent can be incorporated into sustained-release preparations and formulations.

The language "pharmaceutically acceptable carrier" is intended to include solvents, dispersion media, coatings, antibacterial and antifingal agents, isotonic and absorption delaying agents, and the like. The use of such media and agents for pharmaceutically active substances is well known in the art. Except insofar as any conventional media or agent is incompatible with the agent, use thereof in the therapeutic compositions and methods of treatment is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the individual to be treated; each unit containing a predetermined quantity of agent is calculated to produce the desired therapeutic effect in association with the required pharmaceutical carrier. The specification for the novel dosage unit forms of the invention are dictated by and directly dependent on (a) the unique characteristics of the agent and the particular therapeutic effect to be achieve, and (b) the limitations inherent in the art of compounding such an agent for the treatment of *P. aeruginosa* infection in individuals.

The principal agent is compounded for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

The language "an inmmunocompromised host" is intended to include an organism that has an immune system that is incapable of reacting to pathogens. The host can be immunocompromised due to a genetic disorder, disease or drugs that inhibit immune response. An immunocompromised host includes an individual afflicted with cystic fibrosis or who is taking corticosteroids or immunosuppressive agents.

The language "infected with *Pseudomonas aeruginosa*" is intended to include an organism that is found to have the bacteria, *Pseudomonas aeruginosa*, present in its body in an infective form. For example, *Pseudomonas aeruginosa* often infects the lungs of cystic fibrosis patients. Even a small number of *Pseudomonas aeruginosa* found in an organism can constitute infection with *Pseudomonas aeruginosa*.

The present invention further pertains to a culture medium containing as an added compound N-(3-oxododecanoyl) homoserine lactone at a concentration effective to stimulate or promote cellular metabolism, growth or recovery. For example, the culture medium could be used to support growth of *Pseudomonas aeruginosa*.

The language "culture medium" is intended to include a substance on which or in which cells grow. The autoinducer molecule can be included in commercially available cell culture media. Culture media include broths, agar, and gelatin.

The present invention also pertains to a method of regulating the expression of a gene. The method comprises inserting a gene into bacteria chosen for enhancement of gene expression by an agent capable of stimulating the activity of the LasR protein and incubating the bacteria with an agent capable of stimulating the activity of the LasR protein. The method further can include the steps of allowing the gene expression to reach a desired level and then incubating the bacteria with an agent capable of inhibiting the activity of the LasR protein.

The present invention also pertains to a method for detecting the presence or absence of *Pseudomonas aeruginosa* in a sample. The method includes the steps of obtaining a sample fluid suspected of containing *Pseudomonas aeruginosa* and detecting the presence or absence of the autoinducer molecule as an indication of the presence or absence of *Pseudomonas aeruginosa* in the sample. The presence or absence of the autoinducer molecule can be detected using the bioassay described below.

The present invention also pertains to analogs of the autoinducer molecule that inhibit the induction of virulence factors by the autoinducer molecule or LasR. The virulence factors include exotoxin A, elastolytic proteases, and an alkaline protease.

The invention is further illustrated by the following non-limiting examples. The contents of all of the references, published patent applications, and issued patents cited throughout this application are expressly incorporated by reference.

EXAMPLES

Materials And Methods

Bacterial Strains, Plasmids and Culture Conditions

The *E. coli* strains used were TB1 (Gibco-Bethesda Research Laboratories Life Technologies (1984) *Focus* 6, 4), MG4 (Railing, G., Bodrug, S. and Linn, T. (1985) *Mol. Gen. Genet.* 201, 379–386), and VJS533 (Stewart, V. J. and Paroles, J. V., Jr. (1988) *J. Bacteriol.* 170, 1589–1597). The *P. aeruginosa* strains used were PAO1, which contains functional lasR and lasI genes, and PAO-RI, which is a lasR-lasI-mutant derived from PAO1 (Gambello, M. J. and Iglewski, B. H. (1991) *J. Bacteriol.* 173, 3000–3009). The plasmids used were pLasI-1, a lasI expression vector (Passador, L., Cook, J. M., Gambello, M. J., Rust, L. and Iglewski, B. H. (1993) *Science* 260, 1127–1130), pKDT17, which contains a lasB::lacZ reporter of lasB promoter activity and lasR under control of the lac promoter, and pHV200I$^-$, which contains the *V. fischeri* luminescence gene cluster with an inactive luxI. These plasmids are all ColE1 replicons containing an ampicillin-resistance marker. Construction of pKDT17 involved cloning into SmaI-digested pUCP18 (Schweizer, H. P. (1991) *Gene* 97, 109–112) an 800-bp lasR fragment from pMJG1.7 (Gambello, M. J. and Iglewski, B. H. (1991) *J. Bacteriol.* 173, 3000–3009), which extended from the EcoRV site 59-bp upstream of the lasR transcriptional start to the AluI site 22 bp beyond the lasR translational stop codon to construct pKDT11. In this plasmid, lasR is under control of the lac promoter. An intermediate construct containing only two PvuII sites was made by subcloning the 800-bp fragment in pUC18 to form pKDT13. This intermediate construct was digested with PvuII and the plac-lasR fragment was cloned in TthIII-digested pTS400 (Brumlik, M. J. and Storey, D. G. (1992) *Molec. Microbiol.* 6, 337–344). The resulting plasmid was called pKDT17. The plasmid, pHV200I$^-$ was derived from the lux regulon-containing pHV200 (Gray, K. M. and Greenberg, E. P. (1992) *J. Bacteriol.* 174, 4384–4390) by introducing a frameshift mutation in luxI. This was accomplished by digestion of pHV200 with BglII, filling in the single-stranded overhangs with taq polymerase and treating with T4 DNA ligase.

For production of PAI, cultures of *P. aeruginosa* PAO1 or *E. coli* TB1 containing pLasI-1 were grown to the late-logarithmic phase in A medium (Maniatis, T., Fritsch, E. F., and Sambrook, J. (1992) *Molecular Cloning: A Laboratory Manual*, ed. Nolan C. (Cold Spring Harbor Laboratory, Cold Spring Harbor, N.Y.), 2nd Ed) supplemented with 0.4% glucose, 0.05% yeast extract, and 1 mM $MgSO_4$ with shaking at 37° C., unless otherwise specified. For subsequent use in autoinducer bioassays, *E. coli* MG4 containing pKDT17 was grown in supplemented A medium at 30° C. with shaking, and *E. coli* VJS533 containing pHV200I$^-$ was grown in L broth (Silhavy, T. J., Berman, M. L. and Enquist, L. W. (1984) *Experiments with Gene Fusions* (Cold Spring Harbor Lab., Cold Spring Harbor, N.Y.), P. 217) at 30° C. with shaking. For plasmid screening and maintenance, ampicillin (100 µg/ml) was included in *E. coli* cultures, and carbenicillin (200 ug/mi) was included in cultures of *P. aeruginosa*.

Plasmid Purification and Transformation Procedure

Plasmids were purified and manipulated (Maniatis, T., Fritsch, E. F., and Sambrook, J. (1992) *Molecular Cloning: A Laboratory Manual*, ed. Nolan C. (Cold Spring Harbor Laboratory, Cold Spring Harbor, N.Y.), 2nd Ed) as described elsewhere. The transformation procedure used was described by Hanahan (Hanahan, D. (1983) *J. Mol. Biol.* 166, 557–580).

Autoinducer Bioassays

The quantitative assay that was developed for PAI was based on a previous report that *E. coli* MG4 containing a plasmid with lasR and a lasB::lacZ transcriptional fusion showed a 25-fold induction of β-galactosidase, when grown in a medium in which a recombinant *E. coli* containing lasI had been grown previously as compared to a medium in which *E. coli* without lasI had been grown. It has been found that this PAI activity could be extracted and concentrated in ethyl acetate as described for N-(3-oxohexanoyl)homoserine lactone, the *V. fischeri* autoinducer or VAI (Eberhard, A., Burlingame, A. L., Eberhard, C., Kenyon, G. L., Nealson, K. H. and Oppenheimer, N. J. (1981) *Biochemistry* 20, 2444–2449; Nealson, K. H. (1977) *Arch. Microbiol.* 112, 73–79). For the bioassay, overnight cultures of *E. coli* containing the lasB-promoter reporter, pKDT17 were diluted in supplemented A medium to an optical density of 0.1 at 660 nm, and stored on ice. Each bioassay consisted of 2 ml of the cell suspension plus the test sample. After 5.5 h at 30° C. with shaking, β-galactosidase activity was measured by the $CHCl_3$-sodium dodecyl sulfate method described by Miller (Miller, J. A. (1976) *Experiments in Molecular Genetics* (Cold Spring Harbor Lab., Cold Spring Harbor, N.Y.), pp. 352–355). As described in Example 1, there was a linear dose response to autoinducer in this bioassay. Without addition of autoinducer, β-galactosidase activities were 25±10 Miller units, and with saturating amounts of autoinducer, β-galactosidase activities were 1300±200 Miller units. A unit of *P. aeruginosa* autoinducer activity is defined as that amount required to achieve ½-saturation in the bioassay.

The quantitative assay for VAI was based on those described elsewhere (Kaplan, H. B. and Greenberg, E. P. (1985) *J. Bacteriol.* 163, 1210–1214; Bainton, N. J., Bycroft, B. W., Chhabra, S. R., Stead, P., Gledhill, L., Hill, P. J., Rees, C. E. D., Winson, M. K., Salmond, G. P. C., Stewart, G. S. A. B. and Williams, P. (1992) *Gene* 116, 87–91; Nealson, K H. (1977) *Arch. Microbiol.* 112, 73–79). *E. coli* VJS533 containing pHV200I⁻ was used to test for *V.fischeri* autoinducer activity. The plasmid, pHV200I⁻ contains all of the *V. fischeri* genes necessary for autoinducible luminescence in *E. coli*, however, the gene encoding autoinducer synthase, luxI, is inactivated such that *E. coli* containing pHV200I⁻ is not luminescent without addition of VAI. Overnight cultures of *E. coli* containing pHV200I⁻ were diluted to an optical density of 0.01 at 660 nm in an assay medium consisting of 0.05% tryptone, 0.03% glycerol, 100 mM NaCl, 50 mM MgSO$_4$, and 10 mM potassium phosphate, pH 7. Each bioassay consisted of 1 ml of the cell suspension plus the test sample. After 3 hours at room temperature, luminescence was measured by using a Beckman LS 1800 Scintillation Counter that was set for single photon counting. Synthetic VAI (Kaplan, N. B., Eberhard, A., Widrig, C. and Greenberg, E. P. (1985) *J. Radiolabelled Cmpds. and Pharmaceut.* 22, 387–395) was used to construct a standard curve. A unit of activity is defined as that amount required to achieve a half-maximal response [equivalent to approximately 25 nM N-(3-oxohexanoyl) homoserine lactone].

Purification of the *P. aeruginosa* Autoinducer Produced by *E. coli* Containing pLasI-1

The procedure for PAI purification was based on that described previously for purification of VAI (Eberhard, A., Burlingame, A. L., Eberhard, C., Kenyon, G. L., Nealson, K. H. and Oppenheimer, N. J. (1981) *Biochemistry* 20, 2444–2449). Cells and culture fluid were separated by centrifugation (10,000×g for 10 min. at 4° C.). The culture fluid was then passed through a 0.2 μm pore-size filter, and the filtered material was extracted twice with equal volumes of ethyl acetate plus 0.1 ml/liter glacial acetic acid. The combined extracts were pooled, water was removed with magnesium sulfate, and the ethyl acetate was removed by rotary evaporation at 40–45° C. The residue was dissolved in 6 ml of ethyl acetate. The ethyl acetate was removed by rotary evaporation and the residue was then extracted with 5 ml of ethanol. The ethanol solution was was dried by rotary evaporation and the residue was dissolved in ethyl acetate. The ethyl acetate was removed and the residue was extracted in 5 ml of ethanol. This ethanol extract was dried, and dissolved in ethyl acetate. Finally, the sample was dried and dissolved in 0.2 ml of methanol. This sample was further purified by High Performance Liquid Chromatography (HPLC) with a C18 reverse phase column (0.46×25 cm). The *P. aeruginosa* autoinducer activity was first eluted as a sharp peak at 73 to 78% methanol in a linear 20 to 100% gradient of methanol and water. Fractions constituting this peak were pooled, dried by rotary evaporation and the residue dissolved in ethyl acetate plus acetic acid. The ethyl acetate was removed, the residue was dissolved in 0.1 ml of methanol and this solution was subjected to further purification by HPLC, eluting isocratically with 65% methanol in water. Fractions containing autoinducer activity were dried, dissolved in ethyl acetate plus acetic acid and stored at −20° C.

Chemical Synthesis of *P. aeruginosa* Autoinducer

Synthesis of PAI, N-(3oxododecanoyl)-L-homoserine lactone was similar to that described by Eberhard et al (Eberhard, A., Burlingame, A. L., Eberhard, C., Kenyon, G. L., Nealson, K. H. and Oppenheimer, N. J. (1981) *Biochemistry* 20, 2444–2449) for synthesis of the *V. fischeri* autoinducer, N-(3-oxohexanoyl)homoserine lactone. The major difference was that ethyl 3-oxododecanoate was used instead of ethyl 3-oxohexanoate. The ethyl 3-oxododecanoate was prepared from decanoyl chloride and the dilithio dianion of monoethyl hydrogen malonate as described previously (Wierenga, W. and Skulnick, H. K. (1979) *J. Org. Chem.* 44, 310–311). The ethylene glycol ketal of ethyl 3-oxododecanoate was prepared as described for ethyl 3-oxohexanoate (Eberhard, A., Burlingame, A. L., Eberhard, C., Kenyon, G. L., Nealson, K. H. and Oppenheimer, N. J. (1981) *Biochemistry* 20, 2444–2449) except that Dowex-50 sulfonic acid cation exchange resin was used in place of p-toluene sulfonic acid as described by Goswami et al (Goswami, A., Beale, J. M., Jr., Chapman, R. L., Miller, D. W. and Rosazza J. P. (1987) *J. Natural Prod.* 50, 49–54). The sodium salt was prepared as described (Eberhard, A., Burlingame, A. L., Eberhard, C., Kenyon, G. L., Nealson, K. H. and Oppenheimer, N. J. (1981) *Biochemistry* 20, 2444–2449). The sodium 3-oxododecanoate was incubated with equimolar amounts of L-homoserine lactone HCl (Sigma Chemical Co., St. Louis, Mo.) and 1-(3-dimethylaminopropyl)-3-ethylcarbodiimide (Aldrich, Milwaukee, Wis.), and the resulting ethylene glycol ketal of N-(3-oxododecanoyl)-L-homoserine lactone was deprotected by acid treatment (Eberhard, A., Burlingame, A. L., Eberhard, C., Kenyon, G. L., Nealson, K. H. and Oppenheimer, N. J. (1981) *Biochemistry* 20, 2444–2449) to yield N-(3-oxododecanoyl)-L-homoserine lactone. This compound was purified by preparative HPLC using a 20 to 100% methanol gradient as described above. A sharp peak of autoinducer activity eluted at 73 and 78% methanol, exactly where the major peak of natural autoinducer was found to elute. The fractions containing activity were taken to dryness by rotary evaporation, dissolved in ethyl acetate, and this solution was stored at −20° C. prior to further analysis.

Spectra

Proton NMR was performed at the University of Iowa College of Medicine NMR Facility on a Varian Unity 500 MHz instrument. Infrared spectroscopy was performed on a Nicolet 205 FTIR. Chemical ionization mass spectrometry was performed at the University of Iowa College of Medicine Mass Spectrometry Facility on a Nermag RIO-10C instrument with a desorption chemical ionization probe. The reagent gas was ammonia. High-resolution fast atom bombardment was performed at the University of Nebraska—Midwest Center for Mass Spectrometry.

Example 1

Extraction and Purification of PAI from Culture Media

Ethyl acetate extracts of *E. coli* (pLasI-1) culture medium or *P. aeruginosa* PAO1 culture medium contained PAI activity in an amount equivalent to that in the culture medium prior to extraction. Bioassays on extracts of media from cultures grown to an equivalent optical density of 0.3 in supplemented A medium indicated the *P. aeruginosa* culture and the *E. coli* (pLasI-1) culture produced roughly equivalent amounts of PAI (FIG. 1).

Because it has been reported that *P. aeruginosa* produces the *V. fischeri* autoinducer, N-(3-oxohexanoyl)homoserine lactone (Bainton, N. J., Bycroft, B. W., Chhabra, S. R., Stead, P., Gledhill, L., Hill, P. J., Rees, C. E. D., Winson, M. K., Salmond, G. P. C., Stewart, G. S. A. B. and Williams, P. (1992) *Gene* 116, 87–91), this compound was tested for activity as an inducer for the lasB promoter. Also, a homolog of the VAI was tested, N-(3-oxooctanoyl)homoserine lactone, which has recently been reported to serve as the autoinducer in conjugal transfer gene activation in the Gram-negative bacterium, *Agrobacterium tumefaciens*, a plant pathogen (Zhang, L., Murphy, P. J., Kerr, A. and Tate, M. (1993) *Nature* 362, 446–448). VAI had no detectable activity when tested in the *P. aeruginosa* autoinducer bioassay at concentrations as high as 1 uM. This compound gives a maximal response at about 50 nM in the *V. fischeri* autoinducer bioassay. The *A. tumefaciens* autoinducer (AAI), however, did show considerable activity (Table 1). This suggested that PAI was N-(3-oxooctanoyl)homoserine lactone or a compound related to it.

TABLE 1

Influence of *P. aeruginosa*, *V. fischeri*, and *A. tumeficians* Autoinducers on lasB Promoter Activity in *E. coli* MG4 (pKDT17)

| Autoinducer added | β-galactosidase (Miller units)[1] |
|---|---|
| None | 26 +/− 2 |
| 50 nM N-(3-oxohexanoyl)homoserine lactone (VAI) | 33 +/− 3 |
| 500 nM N-(3-oxohexanoyl)homoserine lactone (VAI) | 34 +/− 1 |
| 50 nM N-(3-oxooctanoyl)homoserine lactone (AAI) | 56 +/− 5 |
| 500 nM N-(3-oxooctanoyl)homoserine lactone (AAI) | 733 +/− 50 |
| 1.0 unit *P. aeruginosa* autoinducer[2] | 735 +/− 110 |
| 3.0 units *P. aeruginosa* autoinducer[2] | 1470 +/− 90 |

[1]*P. aeruginosa* autoinducer assay were performed as described in Materials and Methods. β-galactosidase activity is a measure of lasB::lacZ promoter activity. Numbers are the average of four experiments ± the ranges.
[2]The *P. aeruginosa* autoinducer was an ethyl acetate extract of the culture medium in which *E. coli* (pLasI-1) was grown.

Figure 2:
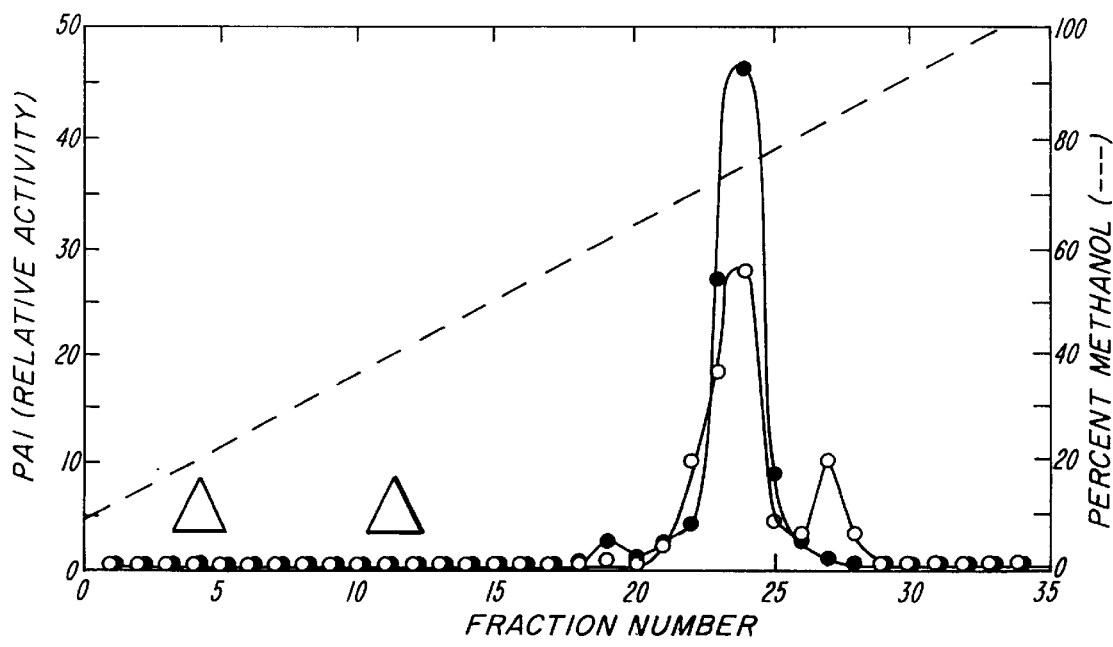
FIG. 2 shows the HPLC analysis of autoinducer extracts. Extracted autoinducer was from an *E. coli* (pLasI-1) culture medium (○), and from a *P. aeruginosa* PAO1 culture medium (●). Methanol-gradient HPLC was as described in *Materials and Methods*. Each fraction was 2 ml. The dashed line indicates the methanol concentration. The percent of activity recovered in the major peak for either bacterium was >75%. The white triangle indicates where N-(3-oxohexanoyl)homoserine lactone elutes, and the black triangle indicates where N-(3-oxo-octanoyl)homoserine lactone elutes.

When PAI from *E. coli* containing pLasI-1 or *P. aeruginosa* PAO1 was subjected to HPLC, a single major peak of activity was observed (FIG. 2). In the case of PAI produced by *E. coli* (pLasI-1) there was a small peak of activity that eluted just after the major peak, and with *P. aeruginosa* there was a small peak of activity that eluted just prior to the major peak. N-(3-oxooctanoyl)homoserine eluted well ahead of the major peak of PAI (FIG. 2). This showed that PAI is not N-(3-oxooctanoyl)homoserine lactone. The *V. fischeri* autoinducer, N-(3-oxohexanoyl)homoserine lactone elutes ahead of N-(3-oxooctanoyl) homoserine lactone. The chromatographic behavior of the PAI, together with the finding that AAI shows activity in the bioassay for *P. aeruginosa* autoinducer suggests that PAI is an N-acyl-homoserine lactone with a hydrophobic side-chain, which is longer than that of AAI.

Because it has been reported that *P. aeruginosa* produces the *V. fischeri* autoinducer (Bainton, N. J., Bycroft, B. W., Chhabra, S. R., Stead, P., Gledhill, L., Hill, P. J., Rees, C. E. D., Winson, M. K., Salmond, G. P. C., Stewart, G. S. A. B. and Williams, P. (1992) *Gene* 116, 87–91), fractions were tested from HPLC for induction of luminescence by using the *V. fischeri* autoinducer bioassay. In fact, there was a peak of activity that eluted at the same location as synthetic N-(3-oxohexanoyl)homoserine lactone. There was also a peak that eluted at the same location as synthetic N-(3-oxooctanoyl)homoserine lactone, which shows some activity with *V. fischeri* (Eberhard, A., Widrig, C., MacBath, P. and Schineller (1986) *Arch. Microbiol.* 146, 35–40), and, as has been shown, is an inducer of the *P. aeruginosa* lasB (Table 1). However, only low levels of these compounds were present in extracts of either *P. aeruginosa* or *E. coli* (pLasI-1) culture media. There was no significant VAI activity in the PAI peaks shown in FIG. 2. Apparently, this *P. aeruginosa* autoinducer cannot cross-react with the *V. fischeri* LuxR protein to activate the luminescence genes.

Example 2

Analysis of Purified *P. aeruginosa* Autoinducer

The level of PAI activity in extracts of *P. aeruginosa* PAO1 medium was similar to the level in extracts of *E. coli* containing pLasI-1 (FIG. 1). The autoinducer produced by *E. coli* containing pLasI-1 was purified because *P. aeruginosa* produces a great variety of extracellular compounds (Nicas, T. I. and Iglewski, B. H. (1985) *Can. J. Microbiol.* 31, 387–392) that could complicate purification of the autoinducer. Using the purification procedure described in the *Materials and Methods*, approximately 300 μg of PAI was obtained from 3 L of culture fluid.

Analysis of the purified PAI by proton NMR in $D_2O$ at 25° C. showed a spectrum that was remarkably similar to that for VAI (Eberhard, A., Burlingame, A. L., Eberhard, C., Kenyon, G. L., Nealson, K. H. and Oppenheimer, N. J. (1981) *Biochemistry* 20, 2444–2449) except that the integrations of the methyl triplet at 0.85 ppm, and the $CH_2$ multiplet at 1.28 ppm indicated the purified PAI had a longer alkyl chain than does VAI. Based on the similarity between the proton NMR spectrum of PAI and VAI, and the ratio of the methyl triplet and the methylene multiplet, it seemed likely that the purified compound was N-(3-oxododecanoyl) homoserine lactone. Chemical ionization mass spectrometry showed a strong quasimolecular $(M+H)^+$ ion with an m/z of 298. This is consistent with the conclusion from the proton NMR analysis that the compound was N-(3-oxododecanoyl) homoserine lactone. The chemical composition was confirmed by high-resolution fast atom bombardment, which more precisely established the mass of the purified compound. The m/z of the $(M+H)^+$ was 298.2018. This corresponded to a chemical composition of $C_{16}H_{27}NO_4$. This is the composition of N-(3-oxododecanoyl)homoserine lactone.

Example 3

Analysis of synthetic N-(3-oxododecanoyl)homoserine lactone

As a confirmation of the conclusion that the purified PAI was N-(3-oxododecanoyl)homoserine lactone, this compound was synthesized. The synthetic compound had chromatographic and spectral properties indistinguishable from those of the material purified from culture medium and was biologically active.

Figure 3:
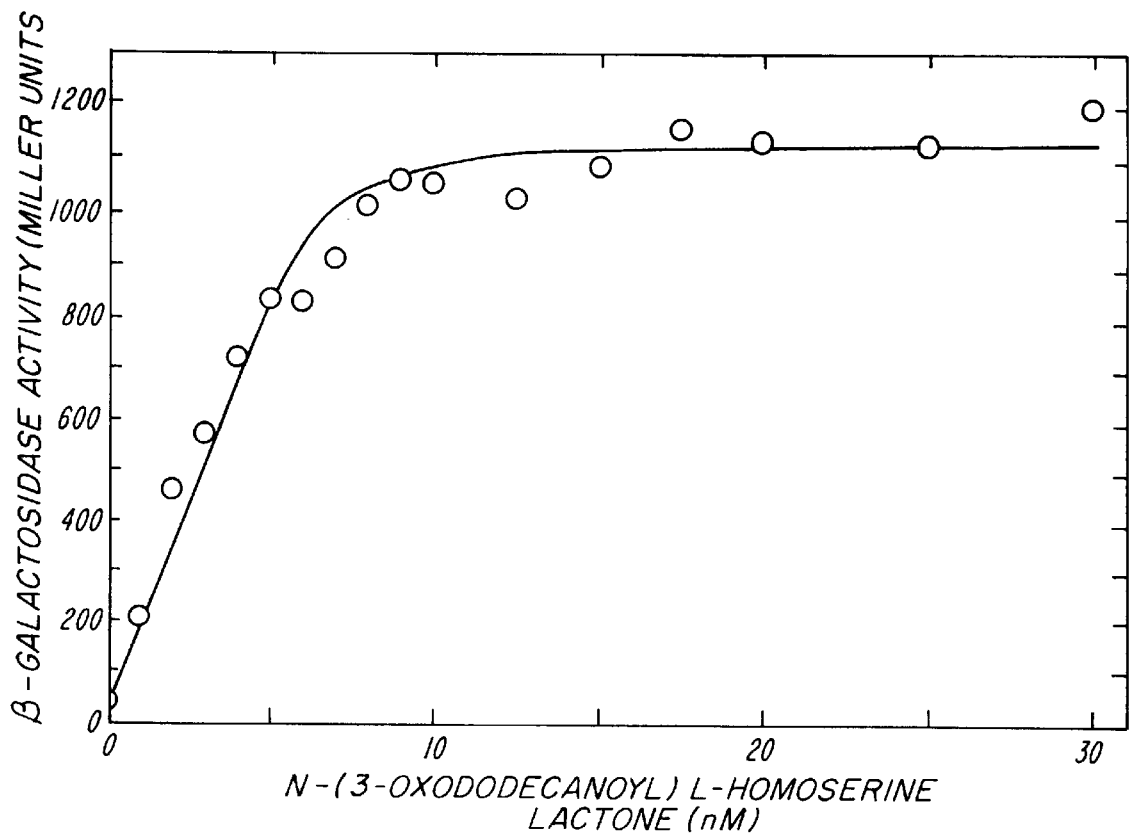
FIG. 3 shows the dose-response curve for activity of synthetic N-(3-oxododecanoyl)homoserine lactone in the *P. aeruginosa* autoinducer bioassay.

The dose response in a *P. aeruginosa* autoinducer bioassay indicates the half-maximal response occurs at 3 to 5 nM N-(3-oxododecanoyl) L-homoserine lactone (FIG. 3). This is in the range found for the *V. fischeri* (Kaplan, H. B. and Greenberg, E. P. (1985) *J. Bacteriol.* 163, 1210–1214) and *A. tumefaciens* (Goswami, A., Beale, J. M., Jr., Chapman, R. L., Miller, D. W. and Rosazza, J. P. (1987) *J. Natural Prod.* 50, 49–54) autoinducer systems where half saturations occur at about 50 nM and 5 nM, respectively.

Discussion

Figure 4:
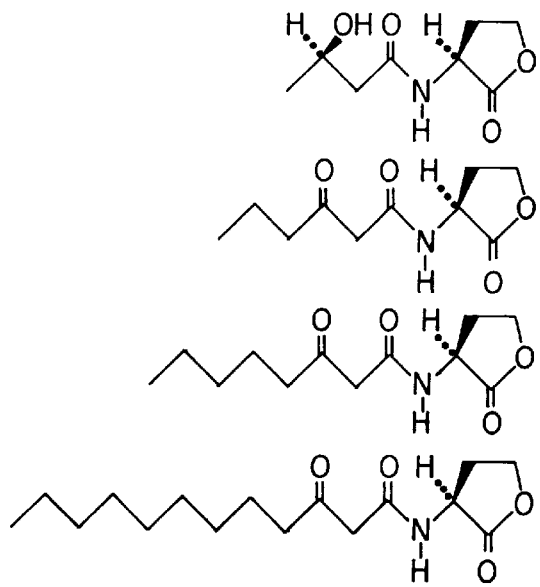
FIG. 4 shows the known autoinducer structures. From the top, N-(3-hydroxybutanoyl)homoserine lactone, the inducer of luminescence in *Vibrio harveyi*; N(3-oxohexanoyl)homoserine lactone, the inducer of *V. fischeri* luminescence; N-(3oxooctanoyl)homoserine lactone, the inducer of conjugal transfer genes in *Agrobacterium tumefaciens*; and N-(3-oxododecanoyl)homoserine lactone, the *P. aeruginosa* autoinducer of the present invention.

Based on the evidence presented in the above examples, the autoinducer, which serves in conjunction with the LasR protein to activate a number of *P. aeruginosa* virulence genes, is N-(3-oxododecanoyl)homoserine lactone. This autoinducer has a longer acyl side chain than related autoinducers from other bacteria (FIG. 4). It was reported elsewhere that *P. aeruginosa* produces the *V. fischeri* autoinducer, N-(3-oxohexanoyl)homoserine lactone (Bainton, N. J., Bycroft, B. W., Chhabra, S. R., Stead, P., Gledhill, L., Hill, P. J., Rees, C. E. D., Winson, M. K., Salmond, G. P. C., Stewart, G. S. A. B. and Williams, P. (1992) *Gene* 116, 87–91), and it was suggested that VAI was the inducer required together with LasR for activation of specific *P. aeruginosa* virulence genes (Jones, S., Yu, B., Bainton, N. J., Birdsall, M., Bycroft, B. W., Chhabra, S. R., Cox, A. J. R., Golby, P., Reeves, P. J., Stephens, S., Winson, M. K., Salmond, G. P. C., Stewart G. S. A. B. and Williams, P. (1993) *EMBO J.* 12, 2477–2482). The analysis performed in the above Examples confirmed that a compound, which serves to induce the *V. fischeri lux* genes is produced by the lasI gene product, and this compound has the behavior of *V. fischeri* autoinducer in HPLC. However, relatively low levels of this compound were synthesized by lasI-containing *P. aeruginosa* or *E. coli* (the concentration of this compound was 0.5% of the PAI concentration in extracts of *P. aeruginosa* PAO1), and neither this compound nor authentic VAI (at concentrations as high as 500 nM) showed *P. aeruginosa* autoinducer activity. In fact, the lasI gene product appears to catalyze the synthesis of a number of related compounds by *E. coli* or *P. aeruginosa*, including compounds that behaved as did N-(3-oxohexanoyl)homoserine lactone and N-(3oxooctanoyl)homoserine lactone when subjected to methanol-water gradient HPLC. However, N-(3-oxododecanoyl)homoserine lactone is the most abundantly produced of these related compounds. Based on the data in FIGS. 1 and 3, approximately 120 ng/ml of this autoinducer was present in a culture of *P. aeruginosa* grown in supplemented A medium as described. This is equivalent to 400 nM PAI, and is in about 40-fold excess of the concentrations required with LasR to fully activate the lasB promoter. In contrast, it is estimated that approximately 0.5 ng/ml of VAI was present in the culture of *P. aeruginosa*.

AAI shows activity not only as the *A. tumefaciens* (Zhang, L., Murphy, P. J., Kerr, A. and Tate, M. (1993) *Nature* 362, 446–448) autoinducer, but also shows activity together with the LuxR protein in activation of *V. fischeri* luminescence genes (Eberhard, A., Widrig, C., MacBath, P. and Schineller (1986) *Arch. Microbiol.* 146, 35–40), and together with the LasR protein in activation of the *P. aeruginosa lasB* (Table 1). The concentration of AAI required for activity as the *P. aeruginosa* autoinducer was higher than the concentration of PAI required for activity, and the maximal response was lower (Table 1, FIG. 3). VAI, N-(3-oxohexanoyl)homoserine lactone, did not show any detectable activity as a *P. aeruginosa* autoinducer (Table 1). Apparently, the LasR protein shows specificity with respect to the N-acyl side chain length. This also has been shown for the *V. fischeri* LuxR protein (Eberhard, A., Widrig, C., MacBath, P. and Schineller (1986) *Arch. Microbiol.* 146, 35–40) and the *A. tumefaciens* TraR (Zhang, L., Murphy, P. J., Kerr, A. and Tate, M. (1993) *Nature* 362, 446–448).

It has recently become apparent that regulatory circuits homologous to the LuxR-LuxI regulatory circuit in *V. fischeri* and the LasR-LasI circuit in *P. aeruginosa* are common to a number of diverse Gram-negative bacteria. At this time, four different autoinducer structures (including PAI as described here) are known (FIG. 4). The luminescence genes in *Vibrio harveyi* are controlled by N-(3-hydroxybutanoyl)homoserine lactone or N-(β-hydroxybutyryl)homoserine lactone (Cao, J.-G. and Merghen, E. A. (1989) *J. Biol. Chem.* 264, 21670–21676; Cao, J.-G. and Meighen, E. A. (1993) *J. Bacteriol.* 175, 3856–3862) but homologs of luxI and luxR in this organism have not been identified. A number of bacteria have been reported to produce N-(3-oxohexanoyl)homoserine lactone, VAI (Bainton, N. J., Bycroft, B. W., Chhabra, S. R., Stead, P., Gledhill, L., Hill, P. J., Rees, C. E. D., Winson, M. K., Salmond, G. P. C., Stewart, G. S. A. B. and Williams, P. (1992) *Gene* 116, 87–91). In one of these bacteria at least, *Erwinia carotovora*, the luxI and luxR homologs expI and expR have been identified (Pirhonen, M., Flego, D., Heikinheimo, R. and Palva, E. T. (1993) *EMBO J.* 12, 2467–2476). The expI gene directs the synthesis of an autoinducer that is required together with the expR product for induction of extracellular protease in a fashion reminiscent of PAI control of extracellular protease induction in *P. aeruginosa*. Conjugal transfer genes in *A. tumifaciens* are controlled by AAI (Zhang, L., Murphy, P. J., Kerr, A. and Tate, M. (1993) *Nature* 362, 446–448) together with a transcriptional activator encoded by traR (Piper, K. R., von Bodman, S. B. and Farrand, S. K. (1993) *Nature* 362, 448–450). The gene or genes required for AAI synthesis have not yet been described.

EQUIVALENTS

Those skilled in the art will recognize, or be able to ascertain using no more than routine experimentation, numerous equivalents to the specific embodiments described herein. Such equivalents are considered to be within the scope of this invention and are covered by the following claims.

What is claimed is:

1. A therapeutic composition comprising an agent which inhibits the activity of the LasR protein of *Pseudomonas aeruginosa* and a pharmaceutically acceptable carrier.

2. The therapeutic composition of claim 1 wherein the agent is a molecule which inhibits the autoinducer activity of N-(3-oxododecanoyl)homoserine lactone.

3. A method of inhibiting the infectivity of *Pseudomonas aeruginosa* comprising administering to an individual a therapeutically effective amount of an agent that inhibits the activity of the LasR protein.

4. A method of treating an immunocompromised individual infected with *Pseudomonas aeruginosa* comprising administering to the individual a therapeutically effective amount of an agent that inhibits the activity of the LasR protein.

5. A method of claim 4 wherein the immunocompromised individual is afflicted with cystic fibrosis.

* * * * *